(12) United States Patent
Bath et al.

(10) Patent No.: US 6,482,814 B1
(45) Date of Patent: Nov. 19, 2002

(54) BIOCIDAL COMPOSITION AND ITS USE

(75) Inventors: Colin Bath, Manchester (GB); John David Payne, Manchester (GB); Paula Louise McGeechan, Manchester (GB)

(73) Assignee: Avecia Limited, Manchester (GB)

( * ) Notice: Subject to any disclaimer, the term of this patent is extended or adjusted under 35 U.S.C. 154(b) by 0 days.

(21) Appl. No.: 09/719,991

(22) PCT Filed: May 18, 1999

(86) PCT No.: PCT/GB99/01579

§ 371 (c)(1),
(2), (4) Date: Feb. 15, 2001

(87) PCT Pub. No.: WO99/65315

PCT Pub. Date: Dec. 23, 1999

(30) Foreign Application Priority Data

Jun. 19, 1998 (GB) .............................................. 9813271

(51) Int. Cl.[7] ........................ A01N 55/02; A61K 31/555
(52) U.S. Cl. ........................ 514/184; 514/185; 514/186; 514/226.5
(58) Field of Search .............................. 514/272, 226.5, 514/184, 185, 186

(56) References Cited

U.S. PATENT DOCUMENTS 4,241,214 A  12/1980  Miller et al.

FOREIGN PATENT DOCUMENTS

| EP | 249 328 | 12/1987 |
| EP | 492 811 | 7/1992 |
| GB | 2 230 190 | 10/1990 |
| WO | WO 92/01380 | 2/1992 |
| WO | 9201380 | * 2/1992 |
| WO | WO 96/22023 | 7/1996 |
| WO | 9622023 | * 7/1996 |

OTHER PUBLICATIONS

Database WPI, Section CH, Week 8244, Derwent Publications Ltd., AN 82–94133E, XPOO2114948 & JP 57 156405 A, Sep. 27, 1982.

* cited by examiner

Primary Examiner—Alton Pryor
(74) Attorney, Agent, or Firm—Pillsbury Winthrop LLP

(57) ABSTRACT

A composition comprising a $C_{3-5}$-alkyl-1,2-benzisothiazolin-3-one and the metal complex of a cyclic thiohydroxamic acid such as the 2:1 zinc salt of either 3-hydroxy-4-methylthiazol-2(3H)-thione or 1-hydroxypyridine-2-thione.

22 Claims, No Drawings

BIOCIDAL COMPOSITION AND ITS USE

This application is a 371 of PCT/G-B99/01579 filed May 18, 1999,

The present invention relates to a biocidal composition comprising a N-alkyl-1,2-benzisothiazolin-3-one and a metal complex of a cyclic thiohydroxamic acid and its use to inhibit the growth of micro-organisms in a medium which is susceptible to microbiological degradation and especially the use to inhibit the growth of deteriogens of plastics materials in soil burial conditions.

WO 96/22023 discloses the use of N-($C_{3-5}$-alkyl)-1,2-benzisothiazolin-3-one as a biocide and especially a fungicide for plastics materials. It has now been found that the antimicrobial activity of these isothiazolinones is significantly improved by incorporating a metal complex of a cyclic thiohydroxamic acid.

According to the invention there is provided a composition comprising (a) a benzisothiazolinone of formula 1 and (b) a metal complex of a cyclic thiohydroxamic acid.

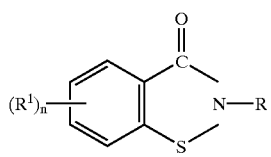

1 wherein
$R^1$ is hydroxy, halogen, $C_{1-4}$-alkyl or $C_{1-4}$-alkoxy;
R is $C_{1-5}$-alkyl, $C_{3-5}$-cycloalkyl or aralkyl; and
n is from 0 to 4.

Preferably, halogen is iodine, bromine and especially chlorine.

When R is alkyl it may be linear or branched and is preferably linear.

When R is cycloalkyl, it is preferably cyclopropyl or cyclopentyl.

When R is aralkyl, it preferably contains two or more carbon atoms in the alkylene group attaching the aryl group to the isothiazolinone ring. Preferably the aralkyl group is 2-phenylethyl. Other examples of aralkyl are benzyl and 2-naphthylethyl.

The substituent $R^1$, when present, is preferably located in the 5 and/or 6 position of the phenyl ring of the benzthiazolinone. However, it is particularly preferred that n is zero.

It is particularly preferred that R is $C_{3-5}$-alkyl, for example n-butyl.

Other examples of suitable benzisothiazolinones are N-methyl-, N-ethyl-, N-n-propyl-, N-isopropyl-, N-n-pentyl-, N-cyclopropyl-, N-isobutyl-, and N-tert-butyl-1,2-benzisothiazolin-3-one.

The cyclic thiohydroxamic acid preferably contains a 5- or 6-membered ring which is optionally substituted. It is preferably a metal complex of a compound of formula 2

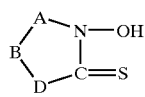

2 wherein
A is a group —$C(R^2)_2$—, —$C(R^2)$= or —$CR^2$=$CR^2$—;
B is a group —$C(R^2)_2$—, —$C(R^2)$= or —$C(NR^2)$—;
D is a group —$C(R^2)_2$—, —$C(R^2)$=, —$NR^2$— or sulphur;

$R^2$ is hydrogen, optionally substituted $C_{1-6}$-hydrocarbyl or two groups $R^2$ together with the carbon atom to which they are attached form a $C_{3-6}$-hydrocarbon ring or two groups $R^2$ together with the two carbon atoms to which they are attached form a fused ring.

When $R^2$ is hydrocarbyl it is preferably alkyl or phenyl and the alkyl group may be branched or preferably linear. It is particularly preferred that $R^2$ is hydrogen or $C_{1-4}$-alkyl, for example methyl.

When $R^2$ is substituted, the substituent may be any group or atom which does not significantly adversely affect the microbiological properties of the cyclic thiohydroxamic ring system. Preferred substituents are hydroxy, halogen and nitrile. It is particularly preferred that $R^2$ is unsubstituted.

When two moieties $R^2$ together with the carbon atom to which they are attached form a ring, the ring is preferably cyclohexyl.

When two moieties $R^2$ together with the carbon atoms to which they are attached form a fused ring, the ring is preferably a fused phenyl ring.

When D is sulphur, the compound of formula 2 is preferably a thiazol-2(3H)-thione wherein both A and B are either the group —$C(R^2)_2$— or especially the group —$C(R^2)$=.

When D is the group —$NR^2$—, the compound of formula 2 is preferably an imidazolidine-2-thione. When D is the group —$NR^2$—, it is also preferred that A is the group —$C(R^2)_2$— or —$C(R^2)$= and B is the group —$C(NR^2)$—.

When D is a group —$C(R^2)_2$— or a group —$C(R^2)$=, it is preferred that both A and B are also the groups —$C(R^2)_2$— or —$C(R^2)$=. In this case, the compound of formula 2 is preferably a pyrrolinethione, pyrrolidinethione or an isoindolinethione.

When A is the group —$CR^2$=$CR^2$—, it is preferably the group —CH=CH— and both B and D are the group —$C(R^2)$= when the compound of formula 2 is a pyridine-2-thione.

Examples of the compound of formula 2 are:

3-hydroxy-4-methylthiazol-2(3H)-thione,
3-hydroxy-4-phenylthiazol-2(3H)-thione,
3-hydroxy-4,5,6,7-tetrahydrobenzothiazol-2(3H)-thione,
5,5-dimethyl-1-hydroxy-4-imino-3-phenylimidazolidine-2-thione,
1-hydroxy-4-imino-3-phenyl-2-thiono-1,3-diazaspiro[4,5]-decane,
1-hydroxy-5-methyl-4-phenylimidazoline-2-thione,
4,5-dimethyl-3-hydroxythiazol-2(3H)-thione,
4-ethyl-3-hydroxy-5-methylthiazol-2(3H)-thione,
4-(4-chlorophenyl)-3-hydroxythiazol-2(3H)-thione,
3-hydroxy-5-methyl-4-phenylthiazol-2(3H)-thione,
1-hydroxypyrrolidin-2-thione,
5,5-dimethyl-1-hydroxypyrrolidin-2-thione,
2-hydroxy-2,3-dihyro-1H-isoindol-1-thione, and
1-hydroxypyridine-2-thione.

The metal which forms the complex of the compound of formula 2 is preferably a metal from Groups IIIA to VA or IB to VIIB or a transition metal of the Periodic Table according to Mendeleef as set out on the inside rear cover of "Handbook of Chemistry and Physics" 49th edition (1968–9) published by The Chemical Rubber Co., Cleveland, Ohio, USA. Preferably, the metal is a metal of Group IIB and is especially zinc.

Particularly useful effects have been obtained when the benzisothiazolinone is N-n-butyl-1,2-benzisothiazolin-3-one and the metal complex of the compound of formula 2 is the 2:1 zinc complex of 3-hydroxy-4-methylthiazol-2(3H)- thione or the 2:1 zinc complex of 1-hydroxypridine-2-thione. The preparation of the benzisothiazolinones is described in GB 484,130 and the preparation of the cyclic thiohydroxamic acids is described in EP 249,328 and U.S. Pat. No. 5,120,856. The preparation of metal complexes of 1-hydroxypyridine-2-thione is specifically disclosed in U.S. Pat. Nos. 2,686,786, 2,758,116 and 2,809,971.

The relative proportions of component (a) and component (b) in the composition can vary between wide limits but is preferably from 100:1 to 1:100, more preferably from 10:1 to 1:10 and especially from 2:1 to 1:2, for example about 1:1.

The composition of the present invention has antimicrobial properties and has been found particularly effective against deteriogens for plastics materials, especially in soil burial applications. Furthermore, the composition according to the present invention exhibits a sum of the Fractional Inhibitory Concentration (hereinafter FIC) for each component which is below 1 and especially below 0.9. The FIC is the ratio of the amount of each component in the composition relative to its Minimum Inhibitory Concentration (MIC) when used alone. Thus, when the FIC is one, the two components exhibit a mere additive effect. When the sum of the FIC values is below one, the mixture is synergistic and when the sum of the FIC values is greater than one, the mixture is antagonistic. The FIC values are preferably determined by constructing an isobologram wherein each component in a matrix array is varied stepwise from a concentration in excess of the MIC down to zero ppm. The isobologram, therefore, allows the smallest value of the sum of the FIC's for each component in the composition to be determined and hence the optimal concentration for each component in the composition.

The composition according to the invention is useful to inhibit the growth of micro-organisms in a medium which is susceptible to microbiological degradation. Component (a) and component (b) of the composition may be added to the medium either sequentially or preferably simultaneously. Where appropriate, the composition may be added directly to the medium, especially where the medium is a solid such as a plastics material. In other uses, it is more convenient to treat the medium with a composition comprising component (a), component (b) and a carrier.

As noted hereinbefore, the composition according to the invention has been found particularly useful as a biocide for inhibiting the growth of deteriogens for plastics materials, especially organic polymeric material containing a plasticiser or stabiliser. Examples of plastics materials are polyurethanes, polyvinylhalides such as polyvinylchloride (PVC), polyalkylenes such as polypropylene, polyalkylene vinyl acetate such as polyethylene vinyl acetate, polyester such as polyethyleneterephthalate, polyamide and polyacrylonitrile. The composition has been found especially effective for inhibiting the growth of micro-organisms in or on plasticised PVC. Other suitable plastics materials are caulks and sealants, especially silicone sealants.

The amount of the composition according to the invention which is present in the plastics material may vary over wide limits from a minimum amount which just inhibits microbiological growth up to many times this amount. Thus, where the plastics material containing the composition is to be used as a master-batch for mixing with untreated plastics material the amount of the composition may be two or three magnitudes greater than that required to inhibit microbiological growth. Preferably, the amount of the composition in the plastics material which is required to inhibit microbial degradation is not less than 10, more preferably not less than 100, even more preferably not less than 500 and especially not less than 1000 ppm relative to the amount of the plastics material. It is also preferred that the amount of the composition which is required to inhibit microbial degradation is not greater than 5000 ppm, more preferably not greater than 4000 ppm and especially not greater than 3000 ppm relative to the amount of the plastics material.

The composition according to the invention may be applied to the plastics material after fabrication to form the finished article but is preferably applied to the plastics material prior to fabrication.

In one preferred method, component (a) and component (b) are applied sequentially or preferably simultaneously to the dry plastics material which may be any solid form such as powder, flake, chip or pellet to form a master-batch. Thus, according to a further aspect of the invention there is provided a master-batch which is a composition comprising a plastics material together with component (a) and component (b).

Where the plastics material is fabricated with a plasticiser or stabiliser, the composition comprising component (a) and component (b) may be conveniently added with a carrier which is a stabiliser and/or plasticiser for a plastics material.

The plasticiser or stabiliser may be any of those commonly used in the plastics material fabrication industry and is preferably a liquid. Examples of suitable plasticiser/stabiliser are esters of aromatic and aliphatic mono- and di-carboxylic acids and linear or branched alcohols especially $C_{8-10}$-alcohols; epoxidised fatty acid esters and epoxidised vegetable oils. Specific examples of plasticisers are di-hexyl-, di-octyl-, di-nonyl, di-isodecyl-, and di-(2-ethylhexyl)- adipates, sebacates, trimellitates and phthalates; epoxidised octyl stearate, epoxidised soya bean oil and phosphate esters of formula $O = P (OR^3)_3$ wherein $R^3$ is hydrocarbyl, particularly phenyl and especially $C_{1-4}$-alkyl and low molecular weight oligo- and poly-esters such as those obtainable by reacting 1,3-butanediol with adipic acid.

According to a still further aspect of the invention there is provided a composition comprising a plasticiser and/or stabiliser for plastics materials together with component (a) and component (b).

As noted hereinbefore, the composition comprising component (a) and component (b) may be conveniently formulated with a carrier which is preferably a non-polar organic liquid, a polar organic liquid or water including mixtures thereof. The metal complex of the cyclic thiohydroxamic acid, which is component (b), is generally insoluble or only sparingly soluble in a carrier such as a non-polar organic liquid, polar organic liquid or water and consequently it is preferable to uniformly distribute the metal complex in the carrier by means of a dispersant. The benzisothiazolinones, which is component (a) of the composition, are mainly liquids and are generally soluble in organic liquids. This is especially true where component (a) is a $C_{1-5}$-alkyl or $C_{3-5}$-cycloalkyl-1,2-benzisothiazolin-3-one. Consequently, for many end-uses, the benzisothiazolinone may be dissolved in the organic liquid without recourse to the use of dispersants. However, when it is desirable to formulate such benzisothiazolinones in water as a carrier it is preferable to uniformly distribute the liquid benzisothiazolinone in the aqueous phase in the presence of an emulsifier. Where component (a) is a solid, such as 2-phenylethyl-1,2-benzisothiazolin-3-one and the carrier is water, it is preferable to use a dispersant.

The choice of dispersant is dependent on the nature of the carrier. Thus, when the carrier is water, the dispersant is preferably anionic or non-ionic. Examples of suitable anionic dispersants are lignin sulphonates and formaldehyde-naphthalene sulphonate condensates. Examples of suitable non-ionic dispersants are polyethers and especially the ethyleneoxidelpropyleneoxide block copolymers, nonylphenolethoxylate, β-naphtholethoxylate, alcohol ethoxylates such as those obtainable from $C_{12-14}$-alcohols, amine ethoxylates and amide ethoxylates. When the carrier is a polar organic liquid, the dispersant is preferably a polyester, especially one obtainable by (co) polymerising a $C_{1-6}$-hydroxyalkylcarboxylic acid or lactone (s) thereof, and where the polyester is subsequently reacted with an amine or polyimine. Other preferred dispersants where the carrier is a polar organic liquid are polyester phosphates and polyisocyanates reacted with polyesters. When the carrier is a non-polar organic liquid, the dispersant is preferably a polyester derivable from a $C_{6-18}$-hydroxyalkylcarboxylic acid which is subsequently reacted with an amine or polyimine and optionally quaternised. Examples of suitable dispersants for non-polar organic liquids are the reaction product of 12-hydroxystearic acid and dimethylaminopropylamine which is quaternised with dimethylsulphate.

As noted hereinbefore, when component (a) is a liquid and the carrier is water it is preferable to formulate component (a) and component (b) in the presence of an emulsifier. Preferred emulsifiers are non-ionic and anionic and include alcohol ethoxy carboxylates, especially those obtainable from $C_{12-14}$-alcohols.

Dispersions containing solid component (b) and/or component (a) (if a solid) can be prepared by any means known to the art and include bead, pebble or ball milling the solid in the liquid carrier until the desired particle size of the solid is attained. Preferably, the particle size is less than 20, more preferably less than 10 and especially less than $5\mu$.

The dispersion may contain other adjuvants which stabilise solids in a liquid carrier. These include adjuvants which provide structure to the liquid carrier and inhibit separation and/or sedimentation of the solid. Where the carrier is an organic liquid, compounds which give structure to the organic liquid are naturally occurring clays such as bentonite and particularly organically treated clays. These organically treated clays are preferably used together with an activator such as mixtures of propylene carbonate and water. The preferred ratio of propylene carbonate to water is 95:5. Where the liquid carrier is water, compounds which give structure to the water are polyacrylamides, alginates and naturally occurring resins, especially Xanthan gum.

The amount of dispersant in the dispersion depends on the type of solid and nature of the liquid carrier but is generally between 1 and 100% and preferably between 5 and 15% based on the amount of solid.

The amount of adjuvant which provides structure to the liquid carrier is preferably from 0.1 to 0.5% based on the total amount of the formulation.

Whereas the composition according to the invention has been found to be particularly useful at inhibiting the growth of deteriogens for plastics materials, it will be readily appreciated that the composition may also be used to protect other media, especially industrial media, which are susceptible to microbiological and especially fungal degradation. Examples of such industrial media are cooling tower liquors, metal working fluids, geological drilling muds, latices, paints, lacquers, wood, leather and pigments. Generally, the amount of the composition required to protect such industrial media is less than that required to protect plastics materials and good protection may be obtained with from 1 to 250 ppm and preferably from 1 to 100 ppm of the composition relative to the medium.

Thus, according to a further aspect of the invention there is provided a method for protecting a medium against microbiological degradation which comprises treating the medium with a composition comprising component (a) and component (b).

The invention is further illustrated by the following examples wherein all references to amount are in parts by weight unless expressed to the contrary.

EXAMPLE 1 a) Determination of MIC

Bacteria were grown to stationary phase (18 hours) in nutrient broth to give approximately $10^9$ colony forming units per ml (CFU/ml). A 0.1% (v/v) inoculum was used to seed fresh medium and 100 $\mu$l was then added to each well of a microtitre plate, except for the first well which contained 200 $\mu$l. By using a doubling dilution technique, the concentration of the chemical under investigation was varied in each well along the ordinate axis. The presence or absence of bacterial growth was determined by visual inspection after 24 hours incubation at 37° C.

A similar technique was used to determine the MIC against fungi except that the fungi were grown on malt agar for 7 days at 25° C. to form a mycelial mat and the spores harvested using physiological saline which was used as inoculum. The presence or absence of fungal growth was determined by visual inspection after incubation for 48 hours at 25° C.

The MIC values (ppm) for the various micro-organisms examined is listed in Table 1 below.

TABLE 1

| Chemical | BBIT | ZO | ZHMT |
| --- | --- | --- | --- |
| Micro-organism | | | |
| Aspergillus niger | 44.5 | 11 | 16 |
| Pseudomonas aeruginosa | 444 | 33.5 | 16 |
| Aureobasidium pullulans | 3 | 1.5 | NT |
| Alternaria alternata | 67 | 55 | NT |

Footnote to Table 1
BBIT is N-n-butyl-1,2-benzisothiazolin-3-one
ZO is 2:1 zinc complex of 1-hydroxypyridine-2-thione
ZHMT is 2:1 zinc complex of 3-hydroxy-4-methylthiazol-2(3H)-thione
NT is not tested.

a) Determination of FIC

A matrix was constructed in a 10×10 array in microtitre wells wherein the concentration of each chemical was varied stepwise by serial dilution from a concentration of twice the MIC down to zero. As each microtitre plate contains only 96 wells the combination of the two compounds making up the extreme concentrations (highest and lowest) were omitted. Each mixture (100 $\mu$l) was added to the plate so that the total volume was maintained at 200 $\mu$l. By transferring 100 $\mu$l from each well to the adjacent well containing 100 $\mu$l nutrient the concentration of the chemical was reduced from twice the MIC to zero in a stepwise manner.

The presence or absence of growth was determined visually after incubation. The plates containing bacteria were incubated for 16–24 hours at 37° C. and the plates containing fungi were incubated for 40–72 hours at 25° C. From the matrix an isobologram was created and the FIC for each chemical of the composition calculated. The FIC is the ratio of the concentration of chemical which inhibits growth when applied as a combination of chemicals relative to the MIC for that chemical when applied alone.

The FIC values for the combination of N-n-butyl-1,2-benzisothiazolin-3-one (BBIT) and the 2:1 zinc complex of 3-hydroxy-4-methylthiazol-2(3H)-thione against a bacterium and a fungus are recorded in Tables 2 and 3, respectively.

TABLE 2

FIC against *Pseudomonas aeruginosa*

| Chemical | | | | | |
|---|---|---|---|---|---|
| BBIT | 0 | 0.25 | 0.49 | 0.76 | 1 |
| ZHMT | 1 | 0.66 | 0.50 | 0.33 | 0 |
| Sum of FIC | 1 | 0.91 | 0.99 | 1.09 | 1 |

Footnote to Table 2
BBIT and ZHMT are as described in the footnote to Table 1.

The data in Table 2 illustrates marked synergy between BBIT and ZHMT relating to Pseudomas aeruginosa and that the optimal composition is 111 ppm BBIT and 10.6 ppm ZHMT. This may be compared with the MIC values of 444 ppm and 16 ppm, respectively.

TABLE 3

FIC against *Aspergillus niger*

| Chemical | | | | | |
|---|---|---|---|---|---|
| BBIT | 0 | 0.19 | 0.39 | 0.61 | 0.8 |
| ZHMT | 1 | 0.62 | 0.37 | 0.24 | 0.12 |
| Sum of FIC | 1 | 0.81 | 0.76 | 0.85 | 0.92 |

Footnote to Table 3
BBIT and ZHMT are as described in the footnote to Table 1.

The data in Table 3 illustrates that BBIT and ZHMT is markedly synergistic against Aspargillus niger and that the optimal composition contains 17.4 ppm BBIT and 5.9 ppm ZHMT. This may be compared with the MIC values of 44.5 ppm BBIT and 16 ppm ZHMT, respectively.

EXAMPLE 2

The FIC values for N-n-butyl-1,2-benzisothiazolin-3-one and the 2:1 zinc complex of 1-hydroxypyridine-2-thione were determined in similar manner to that described in Example 1. The results are given in Table 4 below.

TABLE 4

| | Optimal | Optimal FIC Concentration (ppm) | | MIC Values (ppm) | |
|---|---|---|---|---|---|
| Micro-organism | Sum of FIC | BBIT | ZO | BBIT | ZO |
| *Aspergilius niger* | 0.87 | 5.3 | 8.3 | 44.5 | 11 |
| *Pseudomonas aeruginosa* | 0.74 | 111 | 16.4 | 444 | 33.5 |
| *Alternaria alternata* | 0.73 | 22 | 22 | 67 | 55 |

Footnote to Table 4
BBIT and ZO are as described in the footnote to Table 1.

The data in Table 4 shows that BBIT and ZO are markedly synergistic against fungi and bacteria.

EXAMPLE 3

Polvinylchioride sheets were prepared by callendaring the following mixture at 160° C.
  100 parts Polyvinylchloride (Evipol SH65/20 ex EVC)
  25 parts Dioctylphthalate (ex BP Chemicals)
  25 parts Dioctyladipate (ex BP Chemicals)
  2 parts Mixed Ca/Zn salt Lankromark LN138 as stabiliser (ex Lankro Chem)
  3 parts Lankroflex ED6 as stabiliser/plasticiser (ex Lankro Chem)
  5 parts Calcium stearate (ex Aldrich)
  0.2 parts Stearic acid (ex Aldrich)

Sheets were fabricated with and without a 1:1 mixture of N-n-butyl-1,2-benzisothiazolin 3-one (BBIT) and the 2:1 zinc complex of 1-hydroxypyridine-2-thione (ZO). The biocide mixture was incorporated in a total amount of 1000 ppm and 3600 ppm.

Strips of the PVC (8 parts, 12.5×5 cm) were weighed to 4 decimal places, folded and buried in potting compost (John Innes No 2) in a plastic humidity chamber. The compost was sprayed with a mixed inoculum of Aureobasidium pullulans, Fusarium enicillium funicularum, Scopulariopsis brevicaulis and Streptoverticillium waksmanii and incubated at 25° C. The PVC strips were examined at 4 weeks intervals when they were cleaned, dried and weighed. The weight loss is recorded in Table 5 below.

TABLE 5

| | | Weight Loss (%) | | | |
|---|---|---|---|---|---|
| | | BBIT | ZO | BBIT/ZO (1:1) | |
| Time (weeks) | Control | 3000 ppm | 3000 ppm | 1000 ppm | 3600 ppm |
| 0 | 0 | 0 | 0 | 0 | 0 |
| 4 | 4.3 | 1.2 | 0.3 | 0.3 | 0.2 |
| 8 | 6.8 | 2.8 | 0.8 | 0.7 | 0.3 |
| 12 | 8.3 | 5.6 | 1.5 | 1.2 | 0.5 |
| 16 | 9.8 | 8.1 | 2.3 | 1.4 | 0.6 |

Footnote to Table 5
BBIT and ZO are as explained in the footnote to Table 1.

EXAMPLE 4

A dispersion of N-n-butyl-1,2-benzisothiazolin-3-one (BBIT) and the 2:1 zinc complex of 1-hydroxypridine-2-thione (ZO) was prepared in di-octylphthalate (DOP) having the following composition:
  5 parts BBIT
  5 parts ZO
  0.5 parts dispersant (Solsperse 17000 ex Zeneca)
  0.2 parts organically modified clay (Bentone 38 ex Rheox Inc.)
  0.05 parts 95:5 ratio of propylene carbonate and water
  to 100 parts with dioctylphthalate.

The ZO was milled in DOP containing dispersant until the particle size was reduced below 5 µl. The BBIT was then added followed by the clay and the mixture subjected to high shear mixing. Finally, the propylene carbonate and water were added and again subjected to high shear mixing. This dispersion is a pale white stable formulation which provides similar inhibition of plastics material deteriogens to that described in Example 3.

Example 5

A stable aqueous emulsion of N-n-butyl-1,2-benzisothiazolin-3-one (BBIT) and the 2:1 zinc complex of 3-hydroxy-4-methylthiazol-2(3H)-thione (ZHMT) was prepared having the following composition:
  5 parts BBIT
  5 parts ZHMT
  0.5 parts ethylene oxide/propylene oxide/ethylene oxide disperant (Synperonic A11, ex ICI)
  1.0 part emulsifier (Atlox 4984 ex ICI)

1.0 part emulsifier (Empicol CED 5S ex Albright and Wilson)

0.4 parts Xanthan gum (Keltrol RD ex Kelco)

to 100 parts with water.

The ZHMT was milled in water (45 parts) containing dispersant until the particle size was reduced below 5μp. The BBIT was emulsified in water (45 parts) containing the two emulsifiers under high shear mixing. Finally the aqueous dispersion was added to the emulsion followed by the Xanthan gum and the whole was thoroughly mixed under high shear. A stable white aqueous formulation was obtained.

What is claimed is:

1. A composition comprising (a) a benzisothiazolinone of formula (1)

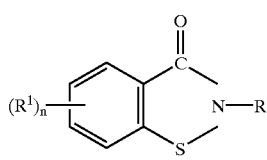

Formula 1 wherein

R$^1$ is hydroxy, halogen, C$_{1-4}$ alkyl, or C$_{1-4}$ alkoxy;

R is C$_{2-5}$ alkyl, C$_{3-5}$ cycloalkyl or aralkyl; and n is from 0 to 4; and (b) a metal complex of a cyclic thiohydroxamic acid containing a pyridine ring or thiazolthione ring, wherein the composition is synergistic.

2. A composition as claimed in claim 1 wherein n is zero.

3. A composition as claimed in either claim 1 or claim 2, wherein R is ethyl, n-propyl, isopropyl, butyl, n-pentyl, isobutyl, tert-butyl, cyclopropyl, cyclopentyl, benzyl or 2-phenylethyl.

4. A composition as claimed in claim 1 or claim 2, wherein the metal complex (b) contains a pyridine ring.

5. A composition as claimed in claim 1 or claim 2, wherein the metal complex (b) contains a thiazolthione ring.

6. A composition as claimed in claim 1, wherein the metal complex (b) is a zinc complex.

7. A composition as claimed in claim 1, wherein component (a) is N-n-butyl-1,2-benzisothiazolin-3-one and component (b) is the 2:1 zinc complex of 3-hydroxy-4-methylthiazol-2(3H)-thione or the 2:1 zinc complex of 1-hydroxypyridine-2-thione.

8. A composition as claimed in claim 1, wherein the ratio of component (a) to component (b) is from 2:1 to 1:2.

9. A composition as claimed in claim 1, which further comprises a plastics material.

10. A composition as claimed in claim 9, wherein the plastics material is polyvinylchloride.

11. A composition as claimed in claim 1 or claim 9, which further comprises a carrier.

12. A composition as claimed in claim 11, wherein the carrier is a plasticiser and/or stabiliser for plastics materials.

13. A composition as claimed in claim 12, wherein the plasticiser and/or stabiliser is diottylphthalate.

14. A composition as claimed in either claim 11 or claim 12, which further comprises a dispersant.

15. A composition as claimed in claim 14, wherein the dispersant is a polyester reacted with an amine or polyimine.

16. A method for protecting a medium against microbiological degradation which comprises treating the medium with a composition as claimed in claim 1.

17. A method for protecting a medium against microbiological degradation which comprises treating the medium with a composition as claimed in claim 4.

18. A method for protecting a medium against microbiological degradation which comprises treating the medium with a composition as claimed in claim 5.

19. A method for protecting a medium against microbiological degradation which comprises treating the medium with a composition as claimed in claim 6.

20. A method for protecting a medium against microbiological degradation which comprises treating the medium with a composition as claimed in claim 7.

21. A method for protecting a medium against microbiological degradation which comprises treating the medium with a composition as claimed in claim 8.

22. A method as claimed in claim 16, wherein the medium is a plastics material.

* * * * *